United States Patent [19]

Takahashi et al.

[11] Patent Number: 5,077,389

[45] Date of Patent: Dec. 31, 1991

[54] CHEMICAL PRODUCT USABLE AS A NON-RADIOACTIVE CARRIER

[75] Inventors: Keietsu Takahashi, Itami; Nobuo Ueda, Kawanishi; Masaaki Hazue, Amagasaki, all of Japan

[73] Assignee: Nihon Medi-Physics Co., Ltd., Hyogo, Japan

[21] Appl. No.: 947,093

[22] Filed: Dec. 29, 1986

Related U.S. Application Data

[62] Division of Ser. No. 558,333, Dec. 5, 1983, Pat. No. 4,666,697.

[30] Foreign Application Priority Data

| Dec. 8, 1982 [JP] | Japan | 57-215857 |
| Dec. 8, 1982 [JP] | Japan | 57-215858 |
| Dec. 8, 1982 [JP] | Japan | 57-215859 |
| Dec. 8, 1982 [JP] | Japan | 57-215860 |

[51] Int. Cl.$^5$ .................... C07K 17/00; A61K 37/24
[52] U.S. Cl. ................................. 530/363; 530/382; 530/388; 530/391; 530/399; 530/409
[58] Field of Search .............. 526/315; 536/1.1, 45, 536/51, 104, 105, 126; 525/380; 530/382, 388, 363, 399, 391

[56] References Cited

U.S. PATENT DOCUMENTS

| 4,287,362 | 9/1981 | Yokoyama et al. . |
| 4,338,248 | 7/1982 | Yokoyama et al. . |
| 4,385,046 | 5/1983 | Milbrath et al. . |
| 4,407,871 | 10/1983 | Eisfeller . |
| 4,425,319 | 1/1984 | Yokoyama et al. . |
| 4,440,739 | 4/1984 | Azuma et al. . |
| 4,474,984 | 10/1984 | Ueda et al. . |
| 4,564,472 | 1/1986 | Ueda et al. . |
| 4,666,697 | 5/1987 | Takahashi et al. .................. 424/1.1 |

*Primary Examiner*—John S. Maples
*Attorney, Agent, or Firm*—Birch, Stewart, Kolasch & Birch

[57] ABSTRACT

The present invention relates to a chemical product usable as a non-radioactive carrier which comprises (1) a unit of a polyformyl compound having at least three formyl groups per molecule, (2) at least two units of an amino group-containing chelating compound bonded to the polyformyl compound by a methyleneimine linkage (—CH=N—) or a methyleneamine linkage (—CH$_2$NH—) between a formyl group in the polyformy compound and an amino group in the chelating compound, optionally followed by reduction, (3) at least one unit of an amino group-containing physiologically active substance bonded to the polyformyl compound by a methyleneimine linkage or a methyleneamine linkage between a formyl group in the polyformyl compound and the amino group in the physiologically active substance, optionally followed by reduction.

21 Claims, No Drawings

CHEMICAL PRODUCT USABLE AS A NON-RADIOACTIVE CARRIER

This application is a divisional of copending application Ser. No. 558,333 filed on Dec. 5, 1983, now U.S. Pat. No. 4,666,697.

The present invention relates to a radioactive diagnostic agent, and non-radioactive carriers therefor. More particularly, it relates to a radioactive diagnostic agent which comprises a formyl group-containing, chelating substance comprising the unit of a polyformyl compound and the unit of an amino group-containing chelating compound in combination, and an amino group-containing physiologically active substance and a radioactive metallic element bonded to said chelating substance, and non-radioactive carriers therefor.

For the purpose of a non-invading (i.e., non-surgical) nuclear medical diagnosis such as recording, dynamic study and quantitative measurement of the blood circulation system, detection of physiological abnormality or localization of abnormality by imaging, there have been widely used physiologically active substances labeled with iodine-131 ($^{131}I$) (i.e., $^{131}I$-labeled serum albumin and $^{131}I$-labeled fibrinogen). However, $^{131}I$ has a long half life of about 8 days and emits betarays so that the patient administered therewith is exposed to a large quantity of radiation.

In order to overcome the above-mentioned drawback in $^{131}I$-labeled physiologically active substances, attempts have been made to provide radioactive diagnostic agents comprising physiologically active substances and radioactive metallic elements having more favorable physical properties than iodine-131. For example, there is a known labeling method wherein a physiologically active substance is directly treated with a radioactive metal salt to make a chelate compound which may be used as a radioactive diagnostic agent. For instance, human serum albumin is treated with an aqueous solution containing technetium-99m ($^{99m}Tc$) in the form of pertechnetate in the presence of a reducing agent to give $^{99m}Tc$-labeled human serum albumin. In another example, bleomycin is treated with an aqueous solution containing indium-111 ($^{111}In$) in the form of indium chloride to give $^{111}In$-labeled bleomycin. However, the chelate forming property of those physiologically active substances is not sufficient and the once formed chelating bond is readily broken. In fact, $^{99m}Tc$-labeled serum albumin and $^{111}In$-labeled bleomycin are so unstable after administration into living bodies that the behavior of the radioactivity in such bodies does not coincide with that of serum albumin or bleomycin of the physiologically active substance. This is a fatal defect for the nuclear medical diagnosis based on the exact trace of the behavior of the radioactivity which should coincide with the behavior of the physiologically active substance.

In recent years, attention was drawn to some chelating compounds which on one hand shown a strong chelate forming property to a variety of metals and on the other hand have an amino group or a carboxyl group highly reactive to various physiologically active substances. Attempts have been made to utilize these characteristic features and combine a radioactive metallic element and a physiologically active substance to them. Examples of such chelating compounds are diethylenetriamine-pentaacetic acid, ethylenediamine-triacetic acid, 3-oxobutyral-bis(N-methylthiosemicarbazone)carboxylic acid, deferoxamine, 3-aminomethylene-2,4-pentanedione-bis(thiosemicarbazone) derivatives, 1-(p-aminoalkyl)phenylpropane-1,2-dionebis(N-methylthiosemicarbazone) derivatives, etc. [Krejcarek: Biochemical & Biophysical Research Comm, Vol. 77, 2, 581–585 (1977); Leurg: Int. J. Appl. Radiation & Isotopes, Vol. 29, 687–692 (1978); Japanese Patent Publn. (unexamined) Nos. 56-34634, 56-125317, 57-102820, etc.]. Since the resulting products are stable and retain the activities of the physiologically active substances combined therein, they are suitable for the diagnostic use. However, the products combined with the physiologically active substances which usually have a large molecular weight such as fibrinogen (molecular weight, about 340,000) and IgG (molecular weight, about 160,000) can hardly provide a sufficiently high radioactivity as necessitated for diagnosis.

In order to overcome the above-mentioned drawback, a combination containing a physiologically active substance having many chelating compounds may be combined with many radioactive metallic elements. While this method will assure high radioactivity, the resulting physiologically active substance may be unfavorably denatured or its physiological activity may be undesirably reduced or lost.

Furthermore, a physiologically active substance having a large molecular weight is preferably administered to human beings at smaller doses in view of its antigen property. For realization of such administration, the physiologically active substance is also preferred to have a higher radio-activity.

As a result of extensive study, it has now been found that the use of a formyl group-containing, chelating substance comprising a unit of a polyformyl compound and a unit of an amino group-containing chelating compound in combination as a carrier for a physiologically active substance and a radioactive metallic element forms a radioactive diagnostic agent. This agent has a relatively high radioactivity per molecule without causing any deterioration or decrease in the physiological activity inherent to the physiologically active substance.

According to the present invention, a radioactive diagnostic agent which comprises (1) a unit of a polyformyl compound having at least three formyl groups per molecule, (2) at least two units of an amino group containing a chelating compound bonded to the polyformyl compound by a methylenimine linkage (—CH=N—) or a methylenamine linkage (—CH$_2$NH—) formed by the condensation between the formyl group in the polyformyl compound and the amino group in the chelating compound, optionally followed by reduction, (3) at least one unit of an amino group-containing a physiologically active substance bonded to the polyformyl compound by a methylenimine linkage or a methylenamine linkage formed by the condensation between the formyl group in the polyformyl compound and the amino group in the physiologically active substance, optionally followed by reduction, and (4) at least two radioactive metallic elements of which each is bonded to the chelating compound through a chelating bond.

A non-radioactive carrier is also provided which comprises (1) a unit of a polyformyl compound having at least three formyl groups, and (2) at least two units of an amino group-containing chelating compound bonded to the polyformyl compound by a methylenimine linkage or a methylenamine linkage which is formed by the condensation between the formyl group in the polyformyl compound and the amino group in the chelating compound, optionally followed by reduction, and being useful for preparation of said radioactive diagnostic agent.

A physiologically active substance which is combined with a non-radioactive carrier is further provided which comprises (1) a unit of a polyformyl compound having at least three formyl groups, (2) at least two units of an amino group-containing chelating compound which is bonded to the polyformyl compound by a methyleimine linkage or a methylenamine linkage formed by the condensation between the formyl group in the polyformyl compound and the amino group in the chelating compound, optionally followed by reduction, and (3) at least one unit of an amino group-containing a physiologically active substance bonded to the polyformyl compound by a methylenimine linkage or a methylenamine linkage which is formed by the condensation between the formyl group in the polyformyl compound and the amino group in the physiologically active substance, optionally followed by reduction, and being useful for preparation of said radioactive diagnostic agent.

The polyformyl compound (1) is required to have at least three formyl groups in the molecule and preferably has a higher number of formyl groups. Among those formyl groups, at least two are combined with a corresponding number on the amino group-containing chelating compound (2), and at least one is combined with a corresponding number on the physiologically active substance (3). Specific examples of the polyformyl compound (1) include polyacrolein, polymethacrolein, etc. The preferred compound is polyacrolein of the formula:

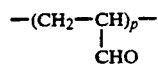

wherein p is usually from 3 to 4,000 and preferably from 10 to 500. The polyacrolein may be prepared, for instance, by subjecting acrolein to Redox polymerization [Schulz et al.: Makromol. Chem. Vol. 24, page 141 (1975)]. Other specific examples include poly(dialdehydosaccharides), and a typical one is a dialdehydostarch of the formula:

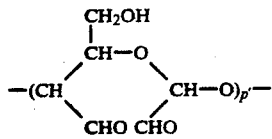

wherein p' is usually from 2 to 1000, preferably from 10 to 500. These may be prepared, for instance, by oxidizing polysaccharides (e.g. starch, amylose, dextran, purdan) with an oxidizing agent (e.g. sodium periodate) so as to form two formyl groups in each saccharide unit.

The amino group-containing chelating compound (2) may be any such compound showing a strong chelate forming property to a radioactive metallic element and has an amino group capable of reacting to a formyl group in the polyformyl compound (1) under a relatively mild condition. Specific examples are deferoxamine (i.e. 1-amino-6,17-dihydroxy-7,10,18,21-tetraoxo-27-(N-acetyl-hydroxylamino)-6,11,17,22-tetraazaheptaeicosane) [The Merck Index, 9th Ed., page 374 (1976)], 3-aminomethylene-2,4-pentanedione-bis(thiosemicarbazone) derivatives of the formula:

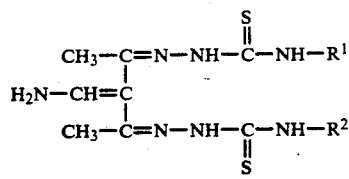

wherein $R^1$ and $R^2$ are each a hydrogen atom, a $C_1$-$C_3$ alkyl group or a phenyl group [EP-A-0054920], 1-(p-aminoalkyl)phenylpropane-1,2-dione-bis(thiosemicarbazone) derivatives of the formula:

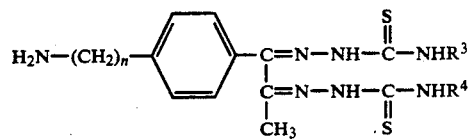

wherein $R^3$ and $R^4$ are each a hydrogen atom or a $C_1$-$C_3$ alkyl group and n is 0 or an integer of 1 to 3 [Australian patent 533722], etc.

Any compound which has a metal capturing property to form a chelate and does not have an amino group but can be readily modified so as to have an amino group or an amino group-containing function is also usable as the chelating compound (2) after the modification. For instance, one compound bearing a carboxyl group may be reacted with hexanediamine so that it is converted into one bearing an aminohexylaminocarbonyl group which can be readily condensed with a formyl group. Specific examples are diethylenetriamine-pentaacetic acid, ethylenediaminetriacetic acid, 2-oxopropionaldehyde-bis(thiosemicarbazone) derivatives of the formula:

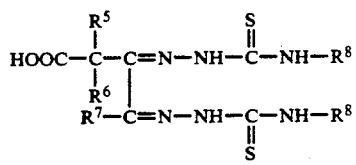

wherein $R^5$, $R^6$, $R^7$ and $R^8$ are each a hydrogen atom or a $C_1$-$C_3$ alkyl group [U.S. Pat. No. 4,287,362].

The term "physiologically active substance" as the constituent (3) is intended to mean any substance which shows a specific accumulability at a certain organ or tissue or a certain diseased locus or exhibits a specific behavior corresponding to a certain physiological state. Tracing of the behavior of such substance in a living body can provide informations useful for diagnosis. Physiologically active substances having an amino group capable of being condensed with a formyl group under a relatively mild condition are advantageously useful in this invention. Even when an amino group is not present, however, the substance may be used as the physiologically active substance (3) after a chemical modification so as to have an amino group or an amino group-containing function. Specific examples of suitable physiologically active substances are blood proteins (e.g. human serum albumin, fibrinogen), enzymes (e.g. urokinase, streptokinase), hormones (e.g. thyroid stimulating hormone, parathyroid hormone), immune antibodies (e.g. IgG), monoclonal antibodies, antibiotics (e.g. bleomycin, kanamycin), saccharides, fatty acids, amino acids, etc. In general, this invention is favorably applicable to physiologically active substances having a molecular weight of not less than about 100,000.

The term "radioactive metallic element" as the constituent (4) is intended to mean any metallic element having radioactivity and has physical characteristics suitable for nuclear medical diagnosis and can be readily captured with the chelate forming structure in the chelating compound (2). Specific examples of the radioactive metallic element are gallium-67 ($^{67}Ga$), gallium-68 ($^{68}Ga$), thallium-201 ($^{201}Tl$), indium-111 ($^{111}In$), tecnethium-99m ($^{99m}Tc$), etc. They are normally employed in their salt form, particularly in their water-soluble salt forms.

For preparation of the non-radioactive carrier of the invention, the polyformyl compound (1) and the chelating compound (2) are subjected to condensation to form a methyleneimine linkage between the formyl group in the former and the amino group in the latter, optionally followed by reduction of the methyleneimine linkage to the methyleneamine linkage. Depending on the kinds of the reactants, the reaction conditions, etc., the number of the units of the chelating compound (2) to be introduced into the polyformyl compound (1) is varied, and generally a larger number of not less than about 5 units, especially of not less than about 10 units, of the chelating compound (2) per each molecule of the polyformyl compound (1) is better, but at least one formyl group in the polyformyl compound (1) should be left for combination with the physiologically active substance (3).

The resulting polyformyl compound (1) combined with the chelating compound (2) condensation or condensation-reduction product (hereinafter referred to as "the condensation or condensation-reduction product") as the non-radioactive carrier is then condensed with the physiologically active substance (3), optionally followed by reduction so as to form a methyleneimine group or a methyleneamine group between a formyl group in the polyformyl compound (1) moiety of the former and the amino group in the latter to give the physiologically active substance-combined condensation or condensation-reduction product. The number of units of the physiologically active substance (3) to be introduced into the condensation or condensation-reduction product varies with the kinds of the reactants and the reaction conditions, etc. The desirable number of units is usually less than about 10 units and is preferably not more than 3 units of the physiologically active substance (3) per each molecule of the polyformyl compound (1).

Alternatively, the physiologically active substance-combined condensation or condensation-reduction product may be prepared by first condensing the polyformyl compound (1) with the physiologically active substance (3) to form a methyleneimine linkage between a formyl group in the former and an amino group in the latter, optionally followed by reduction of the methyleneimine linkage to a methyleneamine linkage, to give the physiologically active substance-combined polyformyl compound. The compound is then condensed with the chelating compound (2) to form a methyleneimine linkage between a formyl group in the polyformyl compound moiety of the physiologically active substance-combined polyformyl compound and an amino group in the chelating compound (2), optionally followed by reduction of the methyleneimine linkage to a methyleneamine linkage, whereby the physiologically active substance-combined condensation or condensation-reduction product is obtained. As to the numbers of the units of the chelating compound (2) and of the physiologically active substance (3), the same attention as stated above may be taken.

In the above-mentioned preparation procedures, the optional reduction after the condensation may be accomplished in a single step at the final stage. Further, each of the reactions such as condensation and reduction may be carried out by conventional procedures. Furthermore, in the reduction, a formyl group may be converted into a hydroxymethyl group simultaneously with the conversion of a methyleneimine linkage into a methyleneamine linkage. Usually, the condensation can easily proceed at room temperature. For the reduction, a reductive metal hydride compound such as sodium borohydride is favorably employed as the reducing agent.

At any stage in the above preparation procedures, the reaction product may be optionally purified by conventional methods such as column chromatography, gel permeation and dialysis.

The resulting physiologically active substance-combined condensation or condensation-reduction product may then be labeled with the radioactive metallic element (4) to give a radioactive metallic element-labeled, physiologically active substance-combined condensation or condensation-reduction product which is a radioactive diagnostic agent of the invention.

Depending upon the kind or state of the radioactive metallic element (4), two different labeling procedures may be adopted. When the radioactive metallic element (4) is in a valency state which can form a stable chelate compound, the physiologically active substance-combined condensation or condensation-reduction product may be contacted with the radioactive metallic element (4) in an aqueous medium to form the radioactive metallic element-labeled, physiologically active substance-combined condensation or condensation-reduction product as a radioactive diagnostic agent. This labeling manner may be applied to $^{67}Ga$, $^{111}In$, etc. When the radioactive metallic element (4) is in a valency state which has to be changed for the formation of a stable chelate compound, the physiologically active substance-combined condensation or condensation-reduction product may be contacted with the radioactive metallic element (4) in an aqueous medium in the presence of a reducing agent or an oxidizing agent to form the radioactive metallic element-labeled, physiologically active substance-combined condensation or condensation-reduction product. This labeling manner may be applied to $^{99m}Tc$, etc.

Examples of the reducing agent are stannous salts, i.e. salts of divalent tin ion ($Sn^{++}$). Specific examples are stannous halides (e.g. stannous chloride, stannous fluoride), stannous sulfate, stannous nitrate, stannous acetate, stannous citrate, etc. $Sn^{++}$ ion-bearing resins, e.g. ion-exchange resins charged with $Sn^{++}$ ion, are also suitable.

When, for example, the radioactive metallic element (4) is $^{99m}Tc$, the physiologically active substance-combined condensation or condensation-reduction product may be treated with $^{99m}Tc$ in the form of a pertechnetate in an aqueous medium in the presence of a reducing agent, e.g. a stannous salt. There is no particular requirement concerning the order of the introduction of the above reagents into the reaction system. Usually, however, initial mixing of the stannous salt with the pertechnetate in an aqueous medium should be avoided. The stannous salt may be used in an amount that can sufficiently reduce the pertechnetate.

The radioactive diagnostic agent should have sufficient radioactivity and radioactivity concentration to assure reliable diagnosis. For instance, the radioactive metallic element $^{99m}$Tc may be used in an amount of 0.1 to 50 mCi in about 0.5 to 5.0 ml at the time of administration. The amount of the physiologically active substance-combined condensation or condensation-reduction product should be sufficient to form a stable chelate compound with the radioactive metallic element (4).

The resulting radioactive metallic element-labeled, physiologically active substance-combined condensation or condensation-reduction product is sufficiently stable as a radioactive diagnostic agent, and therefore it may be stored as such and supplied on demand. When desired, the radioactive diagnostic agent may contain any suitable additive such as a pH controlling agent (e.g. an acid, a base, a buffer), a stabilizer (e.g. ascorbic acid) or an isotonizing agent (e.g. sodium chloride).

The radioactive metallic element-labeled, physiologically active substance-combined condensation or condensation-reduction product of this invention is useful for nuclear medical diagnosis. For example, the $^{99m}$Tc or $^{67}$Ga-labeled streptokinase-combined condensation-reduction product may be used for recording and functional measurement of myocardium. Also, the $^{99m}$Tc-labeled human serum albumin-combined condensation or condensation-reduction product can be used for recording, dynamic study and quantitative measurement of the blood circulation system by intravenous administration to the human body. Further, the $^{99m}$Tc-labeled fibrinogen or urokinase-combined condensation or condensation-reduction product may be used for detection and recording of thrombosis as well as the localization of thrombosis, since they accumulate at the locus of thrombosis. Furthermore, the $^{99m}$Tc-labeled streptokinase-combined condensation or condensation-reduction product is useful for determination of the locus of a myocardial infarction. Moreover, the $^{99m}$Tc-labeled thyroid stimulating hormone-combined condensation or condensation-reduction product is useful for the detection and recording of a cancer at the thyroid gland.

The radioactive diagnostic agent of this invention may be administered to a patient in an amount sufficient to produce the radioactivity necessary for examination of a particular organ or tissue, by any appropriate route, but usually through an intravenous route. For instance, the intravenous administration of a $^{99m}$Tc-labeled radioactive diagnostic agent in an amount of about 1 to 3 ml by volume having a radioactivity of about 1 to 20 mCi to a patient is quite suitable for diagnostic purpose.

The advantages of the physiologically active substance-combined condensation or condensation-reduction product of this invention (i.e. the physiologically active substance-combined non-radioactive carrier) may be summarized as follows: (a) it is stable over a long period of time after manufacture; (b) since it can be produced under mild conditions, no unfavorable side reactions such as inactivation, denaturation or decomposition are caused in the physiologically active substance; (c) any physiologically active substance having an amino group can be used as the starting material; (d) even when an amino group is not present, the introduction of such group into a physiologically active substance makes it usable as the starting material; (e) a radioactive metallic element-labeled, physiologically active condensation or condensation-reduction product can be formed by a very simple procedure (e.g. by merely contacting the physiologically active substance-combined condensation or condensation-reduction product with a radioactive metallic element in an aqueous medium). The advantages of the radioactive metallic element-labeled, physiologically active substance-combined condensation or condensation-reduction product used as a radioactive diagnostic agent may be also summarized as follows: (a) it is stable over a long period of time after manufacture; (b) the labeling efficiency with the radioactive metallic element is extremely high (nearly 100%); (c) since the labeling operation is quite simple, no unfavorable side reactions such as inactivation, denaturation or decomposition are caused in the physiologically active substance bonded to the condensation or condensation-reduction product; (d) among various radioactive metallic elements, the most suitable one for the diagnostic purpose may be chosen so that the diagnosis can be improved not only in quantity but also in quality with reduction of the exposure dose.

Practical and presently preferred embodiments of the invention are illustratively shown in the following Examples.

REFERENCE EXAMPLE 1

Preparation of Polyacrolein

Water (50 ml) was charged in a flask and heated under reflux while introducing nitrogen gas therein. After cooling below 20° C., potassium peroxodisulfate (0.475 g) and acrolein (purity, more than 95%) (10 ml) were added thereto. After acrolein was dissolved, a solution of silver nitrate (0.296 g) in water (6 ml) was dropwise added thereto in about 1 minute with vigorous agitation. The reaction was continued for 2.5 hours, during which care was taken to avoid raising the temperature above 20° C. After the reaction was completed, the reaction mixture was added to water (50 ml), whereby the polyacrolein produced was precipitated. The precipitate was collected by filtration, washed with water two times and dispersed in a solution of sodium thiosulfate (0.5 g) in water (50 ml), followed by stirring for 1 hour. The dispersion was filtered to collect the solid material, which was washed with water several times and dried under reduced pressure overnight to obtain polyacrolein.

Polyacrolein (50 mg) as prepared above was dissolved in dimethylsulfoxide (10 ml), sodium borohydride (3 mg) was added thereto, and stirring was continued at room temperature for 1 hour. Ethyl acetate (10 ml) was added to the resulting mixture to precipitate partially reduced polyacrolein. The precipitate was collected by filtration, dissolved in water and subjected to measurement of molecular weight by high speed liquid chromatography under the following conditions:

Column: TSK-3000SW
Solvent: 0.05M Tris-0.15M sodium chloride-hydrochloric acid buffer (pH, 7.4)
Flow rate: 1.0 ml/min Since the partially reduced polyacrolein was eluted at a retention volume of 23.2 ml, the molecular weight of polyacrolein was determined to be about 21,000.

REFERENCE EXAMPLE 2

Preparation of Dialdehydrodextran

To a solution of dextran (average molecular weight, 10,000) (3.24 g) in 0.1M sodium acetate solution (pH, 4.2; 200 ml), 0.1M sodium periodate solution (40 ml) was added, and the resultant mixture was stirred in a dark place overnight. The reaction mixture was placed into a cellulose tube and dialyzed to water for 2 days, followed by lyophilization to obtain dialdehydodextran.

About 50 mg of the above prepared dialdehydodextran was precisely weighed and then in a 0.01M phosphoric acid-0.15M sodium chloride buffer (100 ml). The resulting solution (about 5 ml) was precisely measured, 1/100N iodine solution (5 ml) was added thereto, and 0.15M sodium carbonate solution (1 ml) was further added thereto, followed by allowing the solution stand at room temperature for 1.5 hours. After addition of 0.2N sulfuric acid (2 ml), titration was carried out with 1/100N sodium thiosulfate solution until a colorless, transparent solution was obtained. This titration value was taken as A. In the same manner as above, 0.01M phosphoric acid-0.15M sodium chloride buffer (5 ml) was titrated with 1/100N sodium thiosulfate solution, and the resulting titration value was taken as B. The content of aldehyde groups in 1 mg of the product was calculated according to the following equation:

Aldehyde groups ($\mu$mole/mg) = (A-B) × 10/2W wherein W is the amount of dialdehydrodextran (mg) contained in 5 ml of the sample. As the result, the aldehyde group content in the dialdehydrodextran as prepared above was determined to be 5.1 $\mu$mole/mg.

EXAMPLE 1

(A) Preparation of the Polyacrolein-Deferoxamine Condensation-Reduction Product as a Non-Radioactive Carrier Polyacrolein (molecular weight, 21,000) (500 mg) was dissolved in dimethylsulfoxide (10 ml), and the resultant solution was admixed with a solution of deferoxamine (420 mg) in dimethylsulfoxide (10 ml). The reaction was continued at room temperature for 3 hours. Sodium borohydride (100 mg) was added to the reaction mixture and stirring was continued at room temperature for 1 hour. The resultant mixture was subjected to dialysis to water overnight, followed by gel chromatography under the following conditions:
Carrier: Sephadex G-50
Solvent: Water
Column: diameter, 4.5 cm; height, 50 cm
Flow rate: 2.5 ml/min The polyacrolein-deferoxamine condensation-reduction product was eluted at a volume of 270-400 ml, while the unreacted deferoxamine was eluted at a volume of 550 to 600 ml. The eluate containing the polyacrolein-deferoxamine condensation-reduction product was subjected to lyophilization.

The polyacrolein-deferoxamine condensation-reduction product thus obtained was dissolved in water, ferric chloride was added thereto, and the resultant solution was analyzed by high speed liquid chromatography under the following conditions to determine a retention volume of 21.2 ml:
Column: TSK-3000SW
Solvent: 0.05M Tris-0.15M sodium chloride-hydrochloric acid buffer (pH, 7.4)
Flow rate: 1.0 ml/min
Absorptive wavelength: 420 nm No free deferoxamine was detected. (The retention volume of deferoxamine in the above system is 32.8 ml.)

A definite amount of the polyacrolein-deferoxamine condensation-reduction product as obtained above was dissolved in water and a sufficient amount of an aqueous ferric chloride solution was added thereto to make a 1:1 complex between the deferoxamine moiety in said condensation-reduction product and Fe (III) in said ferric chloride. The reaction mixture was allowed to stand for 1 hour and then subjected to measurement of absorbance at 420 nm, whereby the number of the deferoxamine moieties in said condensation-reduction product was confirmed to be 18.3 per one molecule of polyacrolein. The average molecular weight of said condensation-reduction product was thus calculated to be about 32,000.

Deferoxamine and Fe (III) can still form a 1:1 complex having a maximum absorption at 420 nm, and the $\epsilon_{max}$ value of the complex at 420 nm is $2.63 \times 10^3$.

EXAMPLE 2

(A) Preparation of the Polyacrolein-hexanediamine:3-oxobutyral-bis(N-methylthiosemicarbazone)-carboxylic Acid Condensate Condensation-Reduction Product as a Non-Radioactive Carrier A solution of 3-oxobutyralbis(N-methylthiosemicarbazone)carboxylic acid (hereinafter referred to as "KTS") (132 mg) in dry dioxane (5 ml) was cooled to about 10° C. Tri-n-butylamine (0.12 ml) and isobutyl chloroformate (64 $\mu$l) were added thereto. The resultant mixture was stirred at the same temperature as above for about 50 minutes to obtain a mixed acid anhydride solution. A solution of N-tert-butyloxycarbonyl-1,6-hexanediamine (104 mg) in dry dioxane (2 ml) was added to this solution, and the resultant mixture was stirred at 10° C. for about 15 hours to produce N-tert-butyloxycarbonyl-1,6-hexanediamine:KTS condensate. A few drops of conc. hydrochloric acid were added thereto to make a pH of about 2, whereby the N-tert-butyloxycarbonyl group was eliminated to give a solution of hexanediamine-KTS condensate.

The above solution was added to a solution of polyacrolein (200 mg) in dimethylsulfoxide (5 ml), sodium borohydride (17.2 mg) was added thereto, and the resultant mixture was reacted at room temperature for 3 hours. The reaction mixture was subjected to dialysis by a conventional procedure for 30 hours to eliminate the unreacted reagents and lyophilized to obtain the polyacrolein-hexanediamine:KTS condensate condensation-reduction product useful as a non-radioactive carrier.

The polyacrolein-hexanediamine:KTS condensate condensation-reduction product as above obtained was dissolved in water to make a concentration of 3 mg/ml, and the resulting solution was subjected to an absorbance measurement at 334 nm using water as the control, whereby the number of the KTS moieties in said condensation-reduction product was confirmed to be 21.3 per one molecule of polyacrolein. The average molecular weight of said condensation-reduction product was thus calculated to be about 29,600.

The hexanediamine: KTS condensate still had a maximum absorption at 334 nm, and its $\epsilon_{max}$ value was $4.37 \times 10^4$.

(B) Preparation of the Fibrinogen-Combined Polyacrolein-Hexanediamine:KTS Condensate Condensation-Reduction Product (a Fibrinogen-Combined Non-Radioactive Carrier)

A solution of the non-radioactive carrier obtained in (A) (before lyophilization) (5 ml) was added to a solution of human fibrinogen (250 mg) in a 0.01M phosphate buffer-0.15M aqueous sodium chloride mixture (pH, 8.4) (50 ml), followed by stirring at room temperature for about 3 hours. Sodium borohydride (12.9 mg) was added thereto. The resultant mixture was stirred for about 1 hour. The reaction mixture was dialyzed to 0.01M glucose-0.35M sodium citrate solution at 0° to 4° C. for 24 hours and then passed through a column of Sepharose 4B (diameter, 4.4 cm; height, 50 cm) using 0.01M glucose-0.35M sodium citrate solution as an eluting solvent. The eluate was lyophilized to give the polyacrolein-hexanediamine:KTS condensate condensation-reduction product as cotton-like crystals.

The cotton-like crystals (100 mg) were dissolved in deoxygenated water (160 ml), and 1 mM stannous chloride solution (10 ml) and sodium ascorbate (0.6 g) were added thereto to make a clear solution. The solution was passed through a filter having a pore diameter of 0.45 μm, and the filtrate (1.5 ml) was filled in a vial flushed with nitrogen gas to obtain a fibrinogen-combined non-radioactive carrier. The above operations were effected under a sterile condition.

The fibrinogen-combined non-radioactive carrier as above obtained was a pale yellow, clear solution.

(C) Preparation of the $^{99m}$Tc-Labeled, Fibrinogen-Combined Polyacrolein-Hexanediamine:KTS Condensate Condensation-Reduction Product as a Radioactive Diagnostic Agent To the fibrinogen-combined non-radioactive carrier (1.5 ml) as obtained in (B), a physiological saline solution (1.5 ml) containing $^{99m}$Tc (3.3 mCi) in the form of sodium pertechnetate was added to obtain the $^{99m}$Tc-labeled, figrinogen-combined polyacrolein-hexanediamine:KTS condensate condensation-reduction product useful as a radioactive diagnostic agent.

This solution was pale yellow and transparent.

(D) Properties of the Radioactive Diagnostic Agent as Obtained in (C)

The radioactive diagnostic agent as obtained in (C) was subjected to electrophoresis (1.7 mA/cm; 15 minutes) using Veronal buffer (pH, 8.6) as a developing solvent and a cellulose acetate membrane as an electrophoretic membrane, and scanning was carried out by the use of a radiochromatoscanner. The radioactivity was recognized as a single peak at the locus of 0.5 cm distant from the original line towards the negative side. This locus was the same as that of the coloring band of fibrinogen with Ponceau 3R.

From the above result, it may be said that the radioactive diagnostic agent has a labeling efficiency of nearly 100% and its electric charge is substantially the same as that of fibrinogen.

To the radioactive diagnostic agent as obtained in (C), 0.1M sodium diethylbarbiturate hydrochloride buffer (pH, 7.3) containing 0.05% calcium chloride was added to make a fibrinogen concentration of 1 mg/ml. Thrombin (100 units/ml; 0.1 ml) was added thereto. The resultant mixture was allowed to stand in an ice bath for 30 minutes. The produced fibrinogen clots were completely separated from the liquor, and radioactivity was measured on the clots and also on the liquor. From the obtained results, it was determined that the clottability of the radioactive diagnostic agent is 93% based on the starting fibrinogen.

EXAMPLE 3

(A) Preparation of the Polyacrolein-Deferoxamine Condensation Product as a Non-Radioactive Carrier To a solution of polyacrolein (125 mg) in dimethylsulfoxide (2.5 ml), a solution of deferoxamine (105 mg) in dimethylsulfoxide (2.5 ml) was added, and the resultant mixture was agitated at room temperature for 3 hours to produce a solution containing the polyacrolein-deferoxamine condensation product, which is useful as a non-radioactive carrier.

(B) Preparation of the Fibrinogen-Combined, Polyacrolein-Deferoxamine Condensation Product (a Fibrinogen-Combined Non-Radioactive Carrier)

The non-radioactive carrier (5 ml) as obtained above was added to a solution of human fibrinogen (200 mg) in 0.01M phosphate buffer-0.15M aqueous sodium chloride mixture (pH, 8.4) at 0° to 4° C., followed by stirring at the same temperature as above for about 3 hours. The reaction mixture was dialyzed to 0.01m glucose-0.35M sodium citrate solution at 0° to 4° C. for 24 hours and then passed through a column of Sepharose 4B (diameter, 4.4 cm; height, 50 cm) using 0.01M glucose-0.35M sodium citrate solution as an eluting solvent. The eluate containing the fibrinogen-combined polyacrolein-deferoxamine condensation product was diluted with 0.01M glucose-0.35M sodium citrate solution to make a fibrinogen concentration of 1 mg/ml, and sodium ascorbate was added thereto to make a concentration of 30 mM. The resultant solution (3 ml) was admitted into a vial, followed by lyophilization to obtain a fibrinogen-combined non-radioactive carrier as a cotton-like product. The above operations were effected under a sterile condition.

EXAMPLE 4

(A) Preparation of the Polyacrolein-Deferoxamine Condensation Product (a Non-Radioactive Carrier)

To a solution of polyacrolein (125 mg) in dimethylsulfoxide (2.5 ml), a solution of deferoxamine (105 mg) in dimethylsulfoxide (2.5 ml) was added, and the resultant mixture was agitated at room temperature for 3 hours to obtain a solution containing the polyacrolein-deferoxamine condensation product useful as a non-radioactive carrier.

(B) Preparation of the Fibrinogen-Combined Polyacrolein-Deferoxamine Condensation-Reduction Product (a Fibrinogen-Combined Non-Radioactive Carrier)

The non-radioactive carrier (5 ml) as obtained above was added to a solution of human fibrinogen (200 mg) in 0.01M phosphate buffer-0.15M aqueous sodium chloride mixture (pH, 8.4) at 0° to 4° C., followed by stirring at the same temperature as above for about 3 hours. To the resulting mixture, sodium borohydride (7.0 mg) was added, and stirring was continued at 0° to 4° C. for about 1 hour.

To a portion of the reaction mixture, a solution containing $^{67}$Ga (1 mCi) in the form of gallium chloride was added for labeling, and the resultant solution was subjected to high speed liquid chromatography under the following conditions:
Column: TSK-3000SW
Solvent: 0.05M Tris-0.15M sodium chloride-hydrochloric acid buffer (pH 7.4)
Pressure: 100 kg/cm$^2$
Flow rate: 1.0 ml/min Detection was made on the radioactivity of $^{67}$Ga. The resulting eluted pattern gave three peaks attributable to $^{67}$Ga-labeled fibrinogen, $^{67}$Ga-labeled polyacrolein-deferoxamine condensation-reduction product and $^{67}$Ga-labeled deferoxamine. From the area ratio of the peak due to $^{67}$Ga-labeled polyacrolein-deferoxamine condensation-reduction product and the peak due to $^{67}$Ga-labeled deferoxamine, 18.9 of the deferoxamine moieties were confirmed to combine to one molecule of polyacrolein. Since the number of the deferoxamine moieties in the fibrinogen-combined polyacrolein-deferoxamine condensation-reduction product was confirmed to be 14.8 per one molecule of fibrinogen, the number of fibrinogen bonded to one molecule of polyacrolein was calculated to be about 0.8.

The remainder of the reaction mixture was dialyzed to 0.01M glucose-0.35M sodium cintrate solution at 0° to 4° C. for 24 hours and then passed through a column of Sepharose 4B (diameter, 4.4 cm; height, 50 cm) as an eluting solvent. The eluate containing the fibrinogen-combined polyacrolein-deferoxamine condensation-reduction product was diluted with 0.01M glucose-0.35M sodium citrate solution to make a fibrinogen concentration of 1 mg/ml, and sodium ascorbate was added thereto to make a concentration of 30 mM. The resultant solution (3 ml) was admitted into a vial, followed by lyophilization to obtain a fibrinogen-combined non-radioactive carrier as a cotton-like product. The above operations were effected under a sterile condition.

The fibrinogen-combined non-radioactive carrier as obtained above was dissolved in sterile water to make a fibrinogen concentration of 1 mg/ml, and a sufficient amount of an aqueous ferric chloride solution was added thereto to make a 1:1 complex between the deferoxamine moiety in said non-radioactive carrier and Fe(III) in said ferric chloride solution. The reaction mixture was allowed to stand for 1 hour and then subjected to measurement of absorbance at 420 nm using a solution of said non-radioactive carrier in sterile water as the control, whereby the number of the deferoxamine moieties in said non-radioactive carrier was confirmed to be 14.8 per one molecule of fibrinogen.

(C) Preparation of the $^{67}$Ga-Labeled, Fibrinogen-Combined Polyacrolein-Deferoxamine Condensation-Reduction Product as a Radioactive Diagnostic Agent To the fibrinogen-combined non-radioactive carrier as obtained in (B), an aqueous solution (2 ml) containing $^{67}$Ga (2 mCi) in the form of gallium citrate was added to obtain the $^{67}$Ga-labeled, fibrinogen-combined polyacrolein-deferoxamine condensation-reduction product as a radioactive diagnostic agent.

This solution was pale yellow, transparent and had a pH of about 7.8.

(C') Preparation of the $^{67}$Ga-Labeled, Fibrinogen-Combined Polyacrolein-Deferoxamine Condensation-Reduction Product as a Radioactive Diagnostic Agent The fibrinogen-labeled non-radioactive carrier obtained in (B) was dissolved in sterile water, and human fibrinogen (0.5, 0.75, 1.0, 1.5, 2.0 or 3.0 mg) dissolved in 0.01M phosphate buffer-0.15M aqueous sodium chloride mixture (pH, 8.4) and 1 ml of an aqueous solution containing $^{67}$Ga (1 mCi) in the form of gallium citrate were added thereto. The resulting mixture was allowed to stand at room temperature for 1 hour and then subjected to measurement of labeling rate. In the same manner as above, the labeling rate of $^{67}$Ga-labeled, fibrinogen-combined deferoxamine as prepared by labeling $^{67}$Ga onto fibrinogen-combined deferoxamine was also measured. The results are shown in Table 1.

TABLE 1

| (Labeling efficiency with $^{67}$Ga) | | |
|---|---|---|
| | Labeling rate (%) | |
| Fibrinogen (mg) | Sample 1*[1]) | Sample 2*[2]) |
| 0.5 | 59.3 | — |
| 0.75 | 83.2 | — |
| 1.0 | 97.8 | 17.0 |
| 1.5 | ~100 | — |
| 2.0 | ~100 | 35.2 |
| 3.0 | ~100 | — |
| 6.3 | — | 41.4 |
| 12.6 | — | 70.9 |
| 18.8 | — | 80.6 |
| 25.1 | — | 83.5 |

Note:
*[1])Radioactive diagnostic agent according to the invention.
*[2])$^{67}$Ga-labeled fibrinogen-combined deferoxamine As understood from the above, the non-radioactive carrier of the invention could be labeled with 97.8% of $^{67}$Ga (1 mCi) within 1 hour when 1 mg of fibrinogen was used. The conventional non-radioactive carrier (i.e. fibrinogen-combined deferoxamine) could be labeled only with 17.0% of $^{67}$Ga under the same condition as above. Even when 25.1 mg of fibrinogen were used, the conventional non-radioactive carrier was labeled with 83.5% of $^{67}$Ga at the most. It is thus appreciated that the non-radioactive carrier of the invention can afford a radioactive diagnostic agent having a higher relative radioactivity. Further, the radioactive diagnostic agent is useful in nuclear medical diagnosis aiming at detection of thrombosis.

(D) Properties of the Radioactive Diagnostic Agent as Obtained in (C)

The radioactive diagnostic agent as obtained in (C) was subjected to electrophoresis (1.7 mA/cm; 15 minutes) using Veronal buffer (pH, 8.6) as a developing solvent and a cellulose acetate membrane as an electrophoretic membrane, and scanning was carried out by the use of a radiochromatoscanner. The radioactivity was recognized as a single peak at the locus of 0.5 cm distant from the original line towards the negative side. This locus was the same as that of the coloring band of fibrinogen with Ponceau 3R.

From the above result, it may be said that the radioactive diagnostic agent has a labeling efficiency of nearly 100% and its electric charge is substantially the same as that of fibrinogen.

To the radioactive diagnostic agent as obtained in (C), 0.1M sodium diethylbarbiturate hydrochloride buffer (pH, 7.3) containing 0.05% calcium chloride was added to make a fibrinogen concentration of 1 mg/ml. Thrombin (100 units/ml; 0.1 ml) was added thereto. The resultant mixture was allowed to stand in an ice bath for 30 minutes. The produced fibrinogen clots were completely separated from the liquor, and radioactivity was measured on the clots and also on the liquor. From the results obtained it was determined that the clottability of the radioactive diagnostic agent is 86% based on the starting fibrinogen.

(E) Behaviors of the Radioactive Diagnostic Agent as Obtained in (C) in Rats

The radioactive diagnostic agent as obtained in (C) (0.2 ml) was administered intravenously to each of the female rats of SD strain, and the variations of the blood level and the organ distribution with the lapse of time were recorded. The results are shown in Table 2.

TABLE 2

| | (Distribution in rat body; %/g) | | | |
|---|---|---|---|---|
| | Time after administration (min) | | | |
| Organs | 5 | 30 | 60 | 180 |
| Blood | 8.33 | 6.82 | 6.22 | 4.81 |
| Liver | 1.47 | 1.62 | 1.73 | 1.78 |
| Heart | 0.85 | 0.88 | 1.03 | 0.96 |
| Spleen | 1.21 | 1.15 | 1.32 | 1.34 |
| Large intestine | 0.11 | 0.18 | 0.15 | 0.20 |
| Small intestine | 0.24 | 0.35 | 0.36 | 0.41 |

The extremely high blood level over a long period of time and the figure of distribution into various organs of the radioactive diagnostic agent as shown in Table 2 are quite similar to those of $^{131}$I-labeled fibrinogen as conventionally employed.

(F) Behaviors of the Radioactive Diagnostic Agent as Obtained in (C) in Thrombosed Rabbits Thrombosis was produced in rabbits at the femoral part by the formalin application procedure. The radioactive diagnostic agent (0.5 ml) as obtained in (C) was administered to the rabbits through an ear vein. After 24 hours from the administration, a constant amount of the blood was sampled and the locus of thrombosis was taken out. Radioactivity was measured on the blood and the locus of thrombosis. The radioactivity ratio of the locus of thrombosis to the blood for the same weight was 7.44±3.41 (average in 10 animals±S.D. value).

From the above results, it is understood that the radioactive diagnostic agent as obtained in (C) has the nearly same physiological activity as does fibrinogen. Thus, the radioactive diagnostic agent is useful for nuclear medical diagnosis.

(G) Toxicity of the Radioactive Diagnostic Agent as Obtained in (C)

The radioactive diagnostic agent as obtained in (C) was subjected to attenuation of the radioactivity to an appropriate extent, and the resultant product was administered intravenously to groups of male and female rats of SD strain. Each group consisted of five animals and a dose of 1 ml per 100 grams of the bodyweight (corresponding to 600 times the expected dose to human beings) was administered. Also, to groups of male and female mice of ICR strain, each group consisting of five animals, a dose of 0.5 ml per 1.0 gram of the bodyweight (corresponding to 3,000 times the expected dose to human beings) was administered. As the control, the same volume of a physiological saline solution as above was intravenously administered to separate groups of the same animals as above. The animals were fertilized for 10 days, and the variation in bodyweight during that period was recorded. No significant difference was recognized between the medicated groups and the control groups.

After 10 days from the administration, all the animals were sacrificed and subjected to observation of the abnormality in various organs. But, no abnormality was seen in any of the animals.

From the above results, it may be said that the toxicity of the non-radioactive carrier of the invention is extremely low.

EXAMPLE 5

(A) Preparation of the Dialdehydostarch-Deferoxamine Condensation Product as a Non-Radioactive Carrier Dialdehydostarch (average molecular weight, 7000; oxidation rate, 80%) (1 g) was dissolved in water (40 ml). Separately, deferoxamine (2.4 g) was dissolved in water (30 ml), an equimolar amount of triethylamine (388 mg) was added thereto, and the resultant solution was stirred at room temperature for 10 minutes. Both solutions were combined together and stirred at room temperature for 15 minutes. The reaction mixture was subjected to gel chromatography under the following conditions:

Carrier: Sephadex G-50
Solvent: Water
Column: diameter, 4.5 cm; height, 50 cm
Flow rate: 2.5 ml/min The dialdehydostarch-deferoxamine condensation product was eluted at a volume of 270–430 ml, while the unreacted deferoxamine was eluted at a volume of 550 to 600 ml. The eluate containing the dialdehydostarch-deferoxamine condensation product was subjected to lyophilization.

The dialdehydostarch-deferoxamine condensation product thus obtained was subjected to analysis by high speed liquid chromatography under the following conditions:

Column: TSK-3000SW
Solvent: 0.05M Tris-0.15M sodium chloride-hydrochloric acid buffer (pH, 7.4)
Pressure: 100 kg/cm$^2$
Flow rate: 1.0 ml/min
Absorptive wavelength: 280 nm No free deferoxamine was detected. (The retention volume of deferoxamine in the above system is 32.8 ml.)

EXAMPLE 6

(A) Preparation of the Dialdehydostarch-Deferoxamine Condensation-Reduction Product as a Non-Radioactive Carrier Dialdehydostarch (average molecular weight, 7000; oxidation rate, 80%) (1 g) was dissolved in water (40 ml). Separately, deferoxamine (2.4 g) was dissolved in water (30 ml), an equimolar amount of triethylamine (388 mg) was added thereto, and the resultant solution was stirred at room temperature for 10 minutes. Both solutions were combined together and stirred at room temperature for 15 minutes. Sodium borohydride (167 mg) was added thereto, and stirring was continued at room temperature for about 1 hour. The reaction mixture was subjected to gel chromatography under the following conditions:

Carrier: Sephadex G-50

Solvent: Water
Column: diameter, 4.5 cm; height, 50 cm
Flow rate: 2.5 ml/min

The dialdehydostarch-deferoxamine condensation-reduction product was eluted at a volume of 300-450 ml, while the unreacted deferoxamine was eluted at a volume of 550 to 600 ml. The eluate containing the dialdehydostarch-deferoxamine condensation-reduction product was subjected to lyophilization.

The dialdehydostarch-deferoxamine condensation reduction product thus obtained was subjected to analysis by high speed liquid chromatography under the following conditions:
Column: TSK-3000SW
Solvent: 0.05M Tris-0.15M sodium chloride-hydrochloric acid buffer (pH, 7.4)
Pressure: 100 kg/cm$^2$
Flow rate: 1.0 ml/min
Absorptive wavelength: 280 nm No free deferoxamine was detected. (The retention volume of deferoxamine in the above system is 32.8 ml.)

A definite amount the dialdehydostarch-deferoxamine condensation-reduction product was dissolved in water, and a sufficient amount of an aqueous ferric chloride solution was added thereto to make a 1:1 complex between the deferoxamine moiety in said condensation-reduction product and Fe(III) in said ferric chloride solution. The reaction mixture was allowed to stand for 1 hour and then subjected to measurement of absorbance at 420 nm, whereby it was confirmed that the number of the deferoxamine moieties in said condensation-reduction product is 19.6 per one molecule of dialdehydostarch. The number average molecular weight of said condensation-reduction product was thus calculated to be about 18,000.

Still, deferoxamine and Fe(III) can form a 1:1 complex having a maximum absorption at 420 nm, and the $\epsilon_{max}$ value of the complex at 420 nm is $2.63 \times 10^3$.

EXAMPLE 7

(A) Preparation of the Dialdehydostarch-Hexanediamine:KTS Condendate Condensation-Reduction Product as a Non-Radioactive Carrier A solution of KTS (132 mg) in dry dioxane (5 ml) was cooled to about 10° C. Tri-n-butylamine (0.12 ml) and isobutyl chloroformate (64 ml) were added thereto. The resultant mixture was stirred at the same temperature as above for about 50 minutes to obtain a mixed acid anhydride solution. To this solution, a solution of N-tert-butyloxycarbonyl-1,6-hexanediamine (104 mg) in dry dioxane (2 ml) was added, and the resultant mixture was stirred at 10° C. for about 15 hours to produce N-tert-butyloxycarbonyl-1,6-hexanediamine:KTS condensate. A few drops of conc. hydrochloric acid were added thereto to make a pH of about 2, whereby the N-tert-butyloxycarbonyl group was eliminated to give a solution of hexanediamine-KTS condensate.

The above solution was added to a solution of dialdehydostarch (200 mg) in dimethylsulfoxide (5 ml), sodium borohydride (17.2 mg) was added thereto, and the resultant mixture was reacted at room temperature for 3 hours. The reaction mixture was subjected to dialysis by a conventional procedure for 30 hours to eliminate the unreacted reagents and lyophilized to obtain dialdehydostarch-hexanediamine:KTS condensate condensation-reduction product.

The dialdehydrostarch-hexanediamine:KTS condensate condensation-reduction product as obtained above was dissolved in water to make a concentration of 3 mg/ml, and the resulting solution was subjected to measurement of absorbance at 334 nm using water as the control, whereby it was confirmed that the number of the KTS moieties in said condensation-reduction product is 11.2 per one molecule of dialdehydostarch. The average molecular weight of said condensation-reduction product was thus calculated to be about 11,500.

The hexanediamine:KTS condensate still had a maximum absorption at 334 nm, and its $\epsilon_{max}$ value was $4.37 \times 10^4$.

(B) Preparation of the Fibrinogen-Combined Dialdehydostarch-Hexanediamine:KTS Condensate Condensation-Reduction Product (a Fibrinogen-Combined Non-Radioactive Carrier)

The hexanediamine:KTS condensate solution as obtained in (A) was added to a solution of dialdehydostarch (200 mg) in dimethylsulfoxide (5 ml), and the resultant mixture was stirred at room temperature for about 3 hours. The resulting solution containing the dialdehydostarch-hexanediamine:KTS condensate condensation product (5 ml) was added to a solution of fibrinogen (250 mg) in a 0.01M phosphate buffer-0.15M aqueous sodium chloride mixture (pH, 8.4) (50 ml), followed by stirring at room temperature for about 3 hours. Sodium borohydride (12.9 mg) was added thereto. The resultant mixture was stirred for about 1 hour. The reaction mixture was dialyzed to 0.01M glucose-0.35M sodium citrate solution at 0° to 4° C. for 24 hours and then passed through a column of Sepharose 4B (diameter, 4.4 cm; height, 50 cm) using 0.01M glucose-0.35M sodium citrate solution as an eluting solvent. The eluate was lyophilized to give the dialdehydostarch-hexanediamine:KTS condensate condensation reduction product as cotton-like crystals. The cotton-like crystals (100 mg) were dissolved in deoxygenated water (160 ml), and 1 mM stannous chloride solution (10 ml) and sodium ascorbate (0.6 g) were added thereto to make a clear solution. The solution was passed through a filter having a pore diameter of 0.22 μm, and the filtrate (1.5 ml) was filled in a vial flushed with nitrogen gas to obtain a fibrinogen-combined non-radioactive carrier as a pale yellow, transparent solution. The above operations were effected under a sterile condition.

(C) Preparation of the $^{99m}$Tc-Labeled, Fibrinogen-Combined Dialdehydostarch-Hexanediamine:KTS Condensate Condensation-Reduction Product as a Radioactive Diagnostic Agent To the fibrinogen-combined non-radioactive carrier (1.5 ml) as obtained in (B), there was added a physiological saline solution (1.5 ml) containing $^{99m}$Tc (3.3 mCi) in the form of sodium pertechnetate, followed by stirring for 15 minutes to obtain the $^{99m}$Tc-labeled, figrinogen-combined polyacrolein-hexanediamine:KTS condensate condensation-reduction product useful as a radioactive diagnostic agent. This solution was pale yellow and transparent.

(D) Properties of the Radioactive Diagnostic Agent as Obtained in (C)

The radioactive diagnostic agent as obtained in (C) was subjected to electrophoresis (1.7 mA/cm; 15 minutes) using a Veronal buffer (pH, 8.6) as a developing solvent and a cellulose acetate membrane as an electrophoretic membrane, and scanning was carried out by the use of a radiochromatoscanner. The radioactivity was recognized as a single peak at the locus of 0.5 cm distant from the original line towards the negative side. This locus was the same as that of the coloring band of fibrinogen with Ponceau 3R.

From the above result, it may be said that the radioactive diagnostic agent as obtained in (C) has a labeling efficiency of nearly 100% and its electric charge is substantially the same as that of fibrinogen.

To the radioactive diagnostic agent as obtained in (C), 0.1M sodium diethylbarbiturate hydrochloride buffer (pH, 7.3) containing 0.05% calcium chloride to make a fibrinogen concentration of 1 mg/ml. Thrombin (100 units/ml; 0.1 ml) was added thereto. The resultant mixture was allowed to stand in an ice bath for 30 minutes. The produced fibrinogen clots were completely separated from the liquor, and radioactivity was measured on the clots and also on the liquor. From the obtained results, it was determined that the clottability of the radioactive diagnostic agent is 91% based on the starting fibrinogen.

EXAMPLE 8

(A) Preparation of the Dialdehydrostarch-Deferoxamine Condensation Product as a Non-Radioactive Carrier To a solution of deferoxamine (130 mg) in 0.01M phosphoric acid-0.15M sodium chloride buffer (1.5 ml), triethylamine (99% solution; 27.9 ul) was added, and the resultant mixture was agitated at room temperature for 5 minutes. An aqueous solution of dialdehydrostarch (25 mg/ml; 2 ml) was added thereto. The resulting mixture was stirred at room temperature for 15 minutes to obtain a solution containing the dialdehydrostarch-deferoxamine condensation product which is useful as a non-radioactive carrier.

(B) Preparation of the Fibrinogen-Combined Dialdehydrostarch-Deferoxamine Condensation Product (a Fibrinogen-Combined Non-Radioactive Carrier The non-radioactive carrier (5 ml) as obtained in (A) was added to a solution of human fibrinogen (200 mg) in 0.01M phosphate buffer-0.15M aqueous sodium chloride mixture (pH, 8.4) (30 ml) at 0° to 4° C., followed by stirring at the same temperature as above for about 3 hours. The reaction mixture was dialyzed to 0.01M glucose-0.35M sodium citrate solution at 0° to 4° C. for 24 hours and then passed through a column of Sepharose 4B (diameter, 4.4 cm; height, 50 cm) using 0.01M glucose-0.35M sodium citrate solution as an eluting solvent.

The eluate containing the fibrinogen-combined dialdehydostarch-deferoxamine condensation product was diluted with 0.01M glucose-0.35M sodium citrate solution to make a fibrinogen concentration of 1 mg/ml, and sodium ascorbate was added thereto to make a concentration of 30 mM. The resultant solution (3 ml) was admitted into each vial, followed by lyophilization to obtain a fibrinogen-combined, non-radioactive carrier as a cotton-like product. The above operations were effected under a sterile condition.

EXAMPLE 9

(A) Preparation of the Dialdehydostarch-Deferoxamine Condensation Product as a Non-Radioactive Carrier To a solution of deferoxamine (130 mg) in 0.01M phosphate buffer-0.15M aqueous sodium chloride solution (1.5 ml), triethylamine (99% solution) (27.9 µl) was added, and the resultant mixture was agitated at room temperature for 5 minutes. An aqueous solution of dialdehydrostarch (25 mg/ml; 2 ml) was added thereto, and stirring was continued at room temperature for 15 minutes to obtain a solution containing the dialdehydostarch-deferoxamine condensation product which is useful as a non-radioactive carrier.

(B) Preparation of the Fibrinogen-Combined Dialdehydostarch-Deferoxamine Condensation-Reduction Product (a Fibrinogen-Combined Non-Radioactive Carrier)

The non-radioactive carrier (3.5 ml) as obtained above was added to a solution of fibrinogen (200 mg) in 0.01M phosphate-0.15M aqueous sodium chloride mixture (pH, 8.4) (30 ml) at 0° to 4° C., followed by stirring at the same temperature as above for about 3 hours. To the resulting mixture, sodium borohydride (12.9 mg) was added, and stirring was continued at 0° to 4° C. for about 1 hour for reduction.

To a portion of the reaction mixture, a solution of gallium citrate containing $^{67}$Ga (1 mCi) was added for labeling, and the resultant solution was subjected to high speed liquid chromatography under the following conditions:

Column: TSK-3000SW
Solvent: 0.05M Tris-0.15M sodium chloride-hydrochloric acid buffer (pH 7.4)
Pressure: 100 kg/cm$^2$
Flow rate: 1.0 ml/min Detection was made on the radioactivity of $^{67}$Ga. As a result, the eluted pattern gave three peaks attributable to $^{67}$Ga-labeled fibrinogen, the $^{67}$Ga-labeled dialdehydrostarch-deferoxamine condensation-reduction product and $^{67}$Ga-labeled deferoxamine. From the area ratio of the peak due to $^{67}$Ga-labeled dialdehydrostarch-deferoxamine condensation reduction product and the peak due to $^{67}$Ga-labelled deferoxamine, it was confirmed that 17.4 of the deferoxamine moieties are combined to one molecule of dialdehydrostarch. Since the number of deferoxamine moieties in the fibrinogen-combined dialdehydrostarch-deferoxamine condensation-reduction product was confirmed to be 15.2 per one molecule of fibrinogen, the number of fibrinogen bonded to one molecule of dialdehydrostarch was calculated as about 0.9.

The remainder of the reaction mixture was dialyzed to 0.01M glucose-0.35M sodium cintrate solution at 0° to 4° C. for 24 hours and then passed through a column of Sepharose 4B (diameter, 4.4 cm; height, 50 cm) using the same solution as above as an eluting solvent. The eluate containing the fibrinogen-combined dialdehydostarch-deferoxamine condensation-reduction product was diluted with 0.01M glucose-0.35M sodium citrate solution to make a fibrinogen concentration of 1 mg/ml, and sodium ascorbate was added thereto to make a concentration of 30 mM. The resultant solution (3 ml) was filled in a vial, followed by lyophilization to obtain a fibrinogen-combined non-radioactive carrier as a cotton-like product. The above operations were effected under a sterile condition.

The fibrinogen-combined non-radioactive carrier was dissolved in sterile water to make a fibrinogen concentration of 1 mg/ml, and a sufficient amount of an aqueous ferric chloride solution was added thereto to make a 1:1 complex between the deferoxamine moiety in said non-radioactive carrier and Fe(III) in said ferric chloride solution. The reaction mixture was allowed to stand for 1 hour and then subjected to an absorbance measurement at 420 nm using a solution of said non-radioactive carrier in sterile water as control, whereby the number of the deferoxamine moieties in said non-radioactive carrier was confirmed to be 15.2 per one molecule of fibrinogen.

(C) Preparation of the $^{67}$Ga-Labeled, Fibrinogen-Combined Dialdehydostarch-Deferoxamine Condensation-Reduction Product as a Radioactive Diagnostic Agent To the fibrinogen-combined non-radioactive carrier as obtained in (B), an aqueous solution (2 ml) containing $^{67}$Ga (2 mCi) in the form of gallium citrate was added to obtain the $^{67}$Ga-labeled, fibrinogen-combined dialdehydostarch deferoxamine condensation-reduction product as a radioactive diagnostic agent. This solution was pale yellow, transparent and had a pH of about 7.8.

(C') Preparation of the $^{67}$Ga-Labeled, Fibrinogen-Combined Dialdehydostarch-Deferoxamine Condensation-Reduction Product as a Radioactive Diagnostic Agent The non-radioactive carrier obtained in (B) was dissolved in sterile water, and human fibrinogen (0.5, 0.75, 1.0, 1.5, 2.0 or 3.0 mg) dissolved in a 0.01M phosphoric acid-0.15M sodium chloride buffer (pH, 8.4) and 1 ml of an aqueous solution containing $^{67}$Ga (1 mCi) in the form of gallium citrate were added thereto. The resulting mixture was allowed to stand at room temperature for 1 hour and then subjected to measurement of the labeling rate. In the same manner as above, the labeling rate of $^{67}$Ga-labeled fibrinogen-combined deferoxamine as prepared by labeling $^{67}$Ga onto the fibrinogen-combined deferoxamine was also measured. The results are shown in Table 3.

TABLE 3

| (Labeling efficiency with $^{67}$Ga) | | |
|---|---|---|
| | Labeling rate (%) | |
| Fibrinogen (mg) | Sample 1*[1)] | Sample 2*[2)] |
| 0.5 | 68.4 | — |
| 0.75 | 85.4 | — |
| 1.0 | ~100 | 17.0 |
| 1.5 | ~100 | — |
| 2.0 | ~100 | 35.2 |
| 3.0 | — | — |
| 6.3 | — | 41.4 |
| 12.6 | — | 70.9 |
| 18.8 | — | 80.6 |
| 25.1 | — | 83.5 |

Note:
*[1)]Radioactive diagnostic agent according to the invention.
*[2)]$^{67}$Ga-labeled fibrinogen-combined deferoxamine As understood from the above, the non-radioactive carrier of the invention could be labeled with 100% of $^{67}$Ga (1 mCi) within 1 hour when 1 mg of fibrinogen was used. The conventional non-radioactive carrier (i.e. fibrinogen-combined deferoxamine) could be labeled only with 17.0% of $^{67}$Ga under the same condition as above. Even when 25.1 mg of fibrinogen were used, the conventional non-radioactive carrier is labeled with 83.5% of $^{67}$Ga at most. It is thus appreciated that the non-radioactive carrier of the invention can afford a radioactive diagnostic agent having a higher relative radioactivity. Further, the radioactive diagnostic agent is useful in nuclear medical diagnosis aiming at detection of thrombosis.

(D) Properties of the Radioactive Diagnostic Agent as Obtained in (C)

The radioactive diagnostic agent as obtained in (C) was subjected to electrophoresis (1.7 mA/cm; 15 minutes) using a Veronal buffer (pH, 8.6) as a developing solvent and a cellulose acetate membrane as an electrophoretic membrane, and scanning was carried out by the use of a radiochromatoscanner. The radioactivity was recognized as a single peak at the locus of 0.5 cm distant from the original line towards the negative side. This locus was the same as that of the coloring band of fibrinogen with Ponceau 3R.

From the above result, it may be said that the radioactive diagnostic agent as obtained in (C) has a labeling efficiency of nearly 100% and its electric charge is substantially the same as that of fibrinogen.

To the radioactive diagnostic agent as obtained in (C), a 0.1M sodium diethylbarbiturate hydrochloride buffer (pH, 7.3) containing 0.05% calcium chloride was added to make a fibrinogen concentration of 1 mg/ml. Thrombin (100 units/ml; 0.1 ml) was added thereto. The resultant mixture was allowed to stand in an ice bath for 30 minutes. The produced fibrinogen clots were completely separated from the liquor, and radioactivity was measured on the clots and also on the liquor. From the obtained results, it was determined that the clottability of the radioactive diagnostic agent is 89% based on the starting fibrinogen.

(E) Behaviors of the Radioactive Diagnostic Agent Obtained in (C) in Rats

The radioactive diagnostic agent as obtained in (C) (0.2 ml) was administered intravenously to each of female rats of SD strain, and the variations of the blood level and the organ distribution with the lapse of time were recorded. The results are shown in Table 4.

TABLE 4

| (Distribution in rat body; %/g) | | | | |
|---|---|---|---|---|
| | Time after administration (min) | | | |
| Organs | 5 | 30 | 60 | 180 |
| Blood | 8.74 | 7.08 | 6.62 | 5.34 |
| Liver | 1.45 | 1.32 | 1.05 | 1.03 |
| Heart | 0.90 | 0.89 | 1.40 | 0.98 |
| Spleen | 0.92 | 0.52 | 1.89 | 0.84 |
| Large intestine | 0.18 | 0.11 | 0.17 | 0.29 |
| Small intestine | 0.25 | 1.75 | 0.44 | 0.45 |

The extremely high blood level over a long period of time and the figure of distribution into various organs of the radioactive diagnostic agent as shown in Table 4 are quite similar to those of $^{131}$I-labeled fibrinogen as conventionally employed.

(F) Behaviors of the Radioactive Diagnostic Agent Obtained in (C) in Thrombosed Rabbits Thrombosis was produced in rabbits at the femoral part by the formalin application procedure. The radioactive diagnostic agent (0.5 ml) obtained in (C) was administered to the rabbits through an ear vein. After 24 hours from the intravenous administration, a constant amount of the blood was sampled, and the locus of thrombosis was taken out. Radioactivity was measured on the blood and the locus of thrombosis. The radioactivity ratio of the locus of thrombosis to the blood for the same weight was 8.63±3.83 (average in 10 animals±S.D. value).

From the above results, it is understood that the radioactive diagnostic agent obtained in (C) has the nearly same physiological activity as fibrinogen does. Thus, the radioactive diagnostic agent is useful for nuclear medical diagnosis.

(G) Toxicity of the Radioactive Diagnostic Agent Obtained in (C)

The radioactive diagnostic agent obtained in (C) was subjected to attenuation of the radioactivity to an appropriate extent, and the resultant product was administered intravenously to groups of male and female rats of SD strain. Each group consisted of five animals and a dose of 1 ml per 100 grams of the bodyweight (corresponding to 600 times the expected dose to human beings) was injected. Also to groups of male and female mice of ICR strain, each group consisting of five animals, a dose of 0.5 ml per 1.0 gram of the bodyweight (corresponding to 3,000 times the expected dose to human beings) was administered. As the control, the same volume of a physiological saline solution as above was intravenously administered to separate groups of the same animals as above. The animals were fertilized for 10 days, and the variation in bodyweight during that period was recorded. No significant difference was recognized between the medicated groups and the control groups.

After 10 days from the administration, all the animals were sacrificed and subjected to observation of the abnormality in various organs. No abnormality was seen in any of the animals.

From the above results, it may be said that the toxicity of the non-radioactive carrier of the invention is extremely low.

EXAMPLE 10

(A) Preparation of Dialdehydodextran-Deferoxamine Condensation-Reduction Product as a Non-Radioactive Carrier To a solution of deferoxamine (2.8 g) in water (30 ml), an equimolar amount of triethylamine (432 mg) was added, followed by stirring at room temperature for 10 minutes. The resultant solution was added to a solution of dialdehydodextran (1 g; aldehyde group content, 5.1 μmole/mg) in water (40 ml), followed by stirring at room temperature for 15 minutes. To the reaction mixture, sodium borohydride (167 mg) was added, and stirring was continued at room temperature for about 1 hour. The resulting solution was admitted in a cellulose tube and dialyzed to water for 3 days, followed by gel chromatography under the following conditions:
Carrier: Sephadex G-50
Solvent: water
Column: diameter, 4.5 cm; height, 50 cm
Flow rate: 2.5 ml/min The dialdehydodextran-deferoxamine condensation-reduction product was eluted at a volume of 300 to 450 ml, while the unreacted deferoxamine was eluted at a volume of 550 to 600 ml. The eluate containing said condensation-reduction product was lyophilized.

The lyophilized product was subjected to analysis with high speed liquid chromatography under the following conditions:
Column: TSK-3000SW
Solvent: 0.05M Tris-0.15M sodium chloride-hydrochloric acid buffer (pH, 7.4)
Pressure: 100 kg/cm$^2$
Flow rate: 1.0 ml/min
Absorptive wavelength: 280 nm As a result, said condensation-reduction product was confirmed to show a retention volume of 27.3 ml. No free deferoxamine was detected. (The retention volume of deferoxamine in the above system is 32.8 ml.)

(B) Preparation of the Fibrinogen-Combined Dialdehydrodextran-Deferoxamine Condensation-Reduction Product (a Fibrinogen-Combined, Non-Radioactive Carrier)

Into a solution of dialdehydodextran (127 mg) in a 0.01M phosphate buffer-0.15M aqueous sodium chloride mixture (5 ml), deferoxamine (370 mg) was dissolved, and triethylamine (78.9 μl) was added thereto, followed by stirring at 10° to 15° C. for 20 minutes. The resulting solution was added to a solution of fibrinogen (400 mg) in a 0.01M phosphate buffer-0.15M aqueous sodium chloride solution (40 ml) at 10° to 15° C., followed by stirring at the same temperature as above for about 2 hours. To the reaction mixture, sodium borohydride (12.3 mg) was added, and stirring was continued at 10° to 15° C. for about 1 hour.

The resulting mixture was dialyzed to 0.01M glucose-0.35M sodium citrate solution at 0° to 4° C. for 3 days and then passed through a column of Sepharose CL6B (diameter, 4.4 cm; height, 100 cm) using the same solution as above as a eluting solvent. The eluate was diluted with 0.01M glucose-0.35M sodium citrate solution to make a fibrinogen concentration of 1 mg/ml, and sodium ascorbate was added to make a concentration of 30 mM. The resultant solution (3 ml) was filled in a vial, followed by lyophilization to obtain a cotton-like product, which is useful as a fibrinogen-combined non-radioactive carrier. The above operations were effected under a sterile condition.

(C) Preparation of the $^{67}$Ga-Labeled, Fibrinogen-Combined Dialdehydodestran-Deferoxamine Condensation-Reduction Product as a Radioactive Diagnostic Agent To the fibrinogen-combined non-radioactive carrier obtained in (B), an aqueous solution (2 ml) containing $^{67}$Ga (2 mCi) in the form of gallium citrate was added to obtain the $^{67}$Ga-labeled, fibrinogen-combined dialdehydostarch deferoxamine condensation-reduction product useful as a radioactive diagnostic agent. This solution was pale yellow, transparent and had a pH of about 7.8.

(D) Properties of the Radioactive Diagnostic Agent as Obtained in (C)

The radioactive diagnostic agent as obtained in (C) was subjected to electrophoresis (1.7 mA/cm; 15 minutes) using a Veronal buffer (pH, 8.6) as a developing solvent and a cellulose acetate membrane as an electrophoretic membrane, and scanning was carried out by the use of a radiochromatoscanner. The radioactivity was recognized as a single peak at the locus of 0.5 cm distant from the original line towards the negative side. This locus was the same as that of the coloring band of fibrinogen with Ponceau 3R.

From the above result, it may be said that the $^{67}$Ga-labeled, fibrinogen-combined dialdehydodextran-deferoxamine condensation-reduction product has a labeling efficiency of nearly 100% and its electric charge is substantially the same as that of human fibrinogen.

To the radioactive diagnostic agent as obtained in (C), 0.1M sodium diethylbarbiturate hydrochloride buffer (pH, 7.3) containing 0.05% calcium chloride was added to make a fibrinogen concentration of 1 mg/ml. Thrombin (100 units/ml; 0.1 ml) was added thereto. The resultant mixture was allowed to stand in an ice bath for 30 minutes. The produced fibrinogen clots were completely separated from the liquor, and radioactivity was measured on the clots and also on the liquor. From the obtained results, it was determined that the clottability of the radioactive diagnostic agent is 84% based on the starting fibrinogen.

EXAMPLE 11

(A) Preparation of the Dialdehydostarch-Deferoxamine Condensation Product as a Non-Radioactive Carrier Into a solution of dialdehydostarch (10 mg) in 0.03M phosphate buffer-0.15M aqueous sodium chloride mixture (1.0 ml), deferoxamine (23 mg) was dissolved at room temperature. After addition of triethylamine (5.2 μl), stirring was continued at 12° to 15° C. for 20 minutes to obtain a solution containing the dialdehydostarch-deferoxamine condensation product useful as a non-radioactive carrier.

(B) Preparation of the 19-9 F(ab')$_2$ Fragment-Combined Dialdehydostarch-Deferoxamine Condensation Product (a 19-9 F(ab')$_2$ Fragment-Combined Non-Radioactive Carrier)

The non-radioactive carrier (0.42 ml) as obtained in (A) was added to a physiological saline solution of 19-9 F(ab')$_2$ fragment (i.e. F(ab')$_2$ fragment of monoclonal antihuman colorectal carcinoma antibody 19-9; concentration, 18 mg/ml) (0.55 ml), followed by stirring at 4° to 6° C. for about 2 hours. After addition of sodium borohydride (3 mg), stirring was continued at 4° to 6° C. for about 1 hour. The reaction mixture was dialyzed to 0.05M phosphate buffer-0.15M aqueous sodium chloride mixture (pH, 5.5) at 4° to 6° C. for 24 hours and then passed through a column of Sephadex G-150 Superfine (diameter, 2.2 cm; height, 30 cm) using 0.05M phosphate buffer-0.15M aqueous sodium chloride mixture as an eluting solvent. The resultant solution was diluted with the same solution as the eluting solvent to make a 19-9 F(ab')$_2$ fragment concentration of 0.5 mg/ml, and sodium ascorbate was added thereto to make a concentration of 100 mM, whereby a 19-9 F(ab')$_2$ fragment-combined non-radioactive carrier was obtained as a pale yellow transparent solution.

(C) Preparation of the $^{67}$Ga-Labeled, 19-9 F(ab')$_2$ Fragment-Combined Dialdehydostarch-Deferoxamine Condensation Product as a Radioactive Diagnostic Agent To the 19-9 F(ab')$_2$ fragment-combined non-radioactive carrier (1 ml) as obtained in (A), a solution (0.5 ml) containing $^{67}$Ga (0.5 mCi) in the form of gallium citrate was added to obtain the $^{67}$Ga-labeled, 19-9 F(ab')$_2$ fragment-combined dialdehydostarch-deferoxamine condensation product as a pale yellow transparent solution, which is useful as a radioactive diagnostic agent.

(D) Properties of the Radioactive Diagnostic Agent as Obtained in (C)

The radioactive diagnostic agent as obtained in (C) was subjected to electrophoresis (1 mA/cm, 30 minutes) using Veronal buffer (pH, 8.6) as a developing solvent and a cellulose acetate membrane as an electrophoretic membrane, and scanning was carried out with a radiochromato-scanner. Radioactivity was recognized as a single peak at the locus of 1.1 cm distant from the original line towards the negative side. This locus was the same as the coloring band of the 19-9 F(ab')$_2$ fragment with Ponceau 3R.

From the above result, it is understood that the radioactive diagnostic agent has a labeling rate of nearly 100% and its electrostatic state is substantially equal to that of the 19-9 F(ab')$_2$ fragment.

What is claimed is:

1. A chemical product usable as a non-radioactive carrier, which comprises:
   (1) a unit of a polyformyl compound having 3 to 4000 formyl groups per molecule,
   (2) at least two units of an amino group-containing chelating compound bond to the polyformyl compound by a methyleneimine linkage (—CH=N—) or a methyleneamine linkage (—CH$_2$NH—) between a formyl group in the polyformyl compound and an amino group in the chelating compound, and
   (3) at least one unit of an amino group-containing physiologically active substance bonded to the polyformyl compound by a methyleneimine linkage or a methyleneamine linkage between a formyl group in the polyformyl compound and an amino group in the physiologically active substance, wherein the physiologically active substance has a molecular weight of not less than about 100,000 and is selected from the group consisting of: human serum albumin, fibrinogen, thyroid stimulating hormone, parathyroid hormone, IgG, a monoclonal antibody and F(ab)$_2$ fragment of monoclonal anti-human colorectal carcinoma antibody 19-9.

2. The chemical product according to claim 1, wherein the polyformyl compound is polyacrolein.

3. The chemical product according to claim 1, wherein the amino group containing chelating compound is bonded to the polyformyl compound by the methyleneimine linkage.

4. The chemical product according to claim 1, wherein the amino group containing chelating compound is bonded to the polyformyl compound by the methyleneamine linkage.

5. The chemical product according to claim 1, wherein the amino group containing physiologically active substance is bonded to the polyformyl compound by a methyleneimine linkage.

6. The chemical product according to claim 1, wherein the amino group containing physiologically active substance is bonded to the polyformyl compound by a methyleneamine linkage.

7. The chemical product according to claim 1, wherein the polyformyl compound is polyacrolein and the chemical product contains 2 to 4,000 units of said chelating compound and 1 to 4,000 units of said physiologically active substance.

8. The chemical product according to claim 1, wherein the polyformyl compound is dialdehydrodextran and the chemical product cont  $ 2 to 4,000 units of said chelating compound and 1 to 4,000 units of said physiologically active substance.

9. The chemical product according to claim 1, wherein the polyformyl compound is a polymethacrolein having 10 to 500 repeating units and the chemical product contains 2 to 4,000 units of said chelating compound and 1 to 4,000 units of said physiologically active substance.

10. The chemical product according to claim 1, wherein the polyformyl compound is a polyacrolein having 10 to 500 repeating units.

11. The chemical product according to claim 1, wherein the physiologically active substances have a molecular weight up to about 100,000.

12. The chemical product of claim 1, wherein the physiologically active substance has a molecular weight of not less than 100,000 and is selected from the group consisting of:
human serum albumin, fibrinogen, thyroid stimulating hormone, parathyroid hormone, IgG and F(ab')₂ fragment of monoclonal anti-human colorectal carcinoma antibody 19-9.

13. The chemical product of claim 1, wherein the physiologically active substance is fibrinogen or the F(ab')₂ fragment of monoclonal anti-human colorectal carcinoma antibody 19-9.

14. The chemical product according to claim 1, wherein the polyformyl compound is a poly(dialdehydosaccharide).

15. The chemical product according to claim 14, wherein the product contains 2 to 4,000 units of said chelating compound and 1 to 4,000 units of said physiologically active substance.

16. The chemical product according to claim 14, wherein poly(dialdehydosaccharide) has 10 to 500 repeating units.

17. The chemical product according to claim 14, wherein the poly(dialdehydosaccharide) is dialdehydostarch.

18. The chemical product according to claim 17, wherein the product contains 2 to 4,000 units of said chelating compound and 1 to 4,000 units of said physiologically active substance.

19. The chemical product according to claim 17, wherein the poly(dialdehydosahccaride) is dialdehydodextran.

20. A chemical product usable as a non-radioactive carrier, which comprises:
(1) a unit of a polyformyl compound having 3 to 4000 formyl groups per molecule,
(2) at least two units of an amino group-containing chelating compound bonded to the polyformyl compound by a methyleneimine linkage (—CH=N—) or a methyleneamine linkage (—CH₂NH—) between a formyl group in the polyformyl compound and an amino group in the chelating compound, and
(3) at least one unit of an amino group-containing physiologically active substance bonded to the polyformyl compound by a methyleneimine linkage or a methyleneamine linkage between a formyl group in the polyformyl compound and an amino group in the physiologically active substance, wherein the physiologically active substance is fibrinogen or the F(ab')₂ fragment of monoclonal anti-human colorectal carcinoma antibody 19-9.

21. The chemical product of claim 20, wherein the physiologically active substance is fibrinogen.

* * * * *